United States Patent
Kang et al.

(10) Patent No.: US 11,633,115 B2
(45) Date of Patent: Apr. 25, 2023

(54) APPARATUS AND METHOD FOR ESTIMATING BIO-INFORMATION

(71) Applicant: SAMSUNG ELECTRONICS CO., LTD., Suwon-si (KR)

(72) Inventors: Jae Min Kang, Seoul (KR); Yong Joo Kwon, Yongin-si (KR); Youn Ho Kim, Hwaseong-si (KR); Sang Yun Park, Hwaseong-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 549 days.

(21) Appl. No.: 16/578,546

(22) Filed: Sep. 23, 2019

(65) Prior Publication Data
US 2020/0253485 A1    Aug. 13, 2020

(30) Foreign Application Priority Data
Feb. 7, 2019    (KR) .......................... 10-2019-0014554

(51) Int. Cl.
```
A61B 5/024      (2006.01)
A61B 5/021      (2006.01)
A61B 5/0285     (2006.01)
A61B 5/1455     (2006.01)
A61B 5/00       (2006.01)
G06F 1/16       (2006.01)
```
(52) U.S. Cl.
CPC .............. *A61B 5/024* (2013.01); *A61B 5/021* (2013.01); *A61B 5/0285* (2013.01); *A61B 5/1455* (2013.01); *A61B 5/7278* (2013.01); *G06F 1/163* (2013.01)

(58) Field of Classification Search
None
See application file for complete search history.

(56) References Cited

U.S. PATENT DOCUMENTS

| 8,313,439 B2 | 11/2012 | McCombie et al. |
| 8,485,978 B2 | 7/2013 | Linder |
| 10,398,324 B2 | 9/2019 | Mukkamala et al. |

(Continued)

FOREIGN PATENT DOCUMENTS

| JP | 2016-220886 A | 12/2016 |
| JP | 2017-121410 A | 7/2017 |

(Continued)

OTHER PUBLICATIONS

Teng et al., "Theoretical study on the effect of sensor contact force on pulse transit time", IEEE Transactions on Biomedical Engineering, 2007. (Year: 2007).*
Teng et al., "The effect of contacting force on photoplethysmographic signals," Physiolog. Meas., vol. 25, No. 5, pp. 1323-1335, Oct. 2004. (Year: 2004).*
Rong-Hao Liang et al. "BioFidget: Biofeedback for Respiration Training Using an Augmented Fidget Spinner", ACM SIGCHI Conference on Human Factors in Computing Systems, 2018 (9 pages total).

(Continued)

*Primary Examiner* — Yi-Shan Yang
(74) *Attorney, Agent, or Firm* — Sughrue Mion, PLLC

(57) ABSTRACT

An apparatus for estimating bio-information according to an embodiment includes: a sensor that measures a pulse wave signal from an object and contact pressure of the object; and a processor that obtains an oscillometric envelope based on an amplitude of the pulse wave signal and the contact pressure, and estimates bio-information based on a center of mass of a phase of contact pressure of the obtained oscillometric envelope.

20 Claims, 17 Drawing Sheets

(56) References Cited

U.S. PATENT DOCUMENTS

| | | |
|---|---|---|
| 2005/0119578 A1* | 6/2005 | Kubo .................. A61B 5/0225 600/490 |
| 2010/0274143 A1 | 10/2010 | Kim et al. |
| 2011/0230744 A1 | 9/2011 | Ribas Ripoll et al. |
| 2013/0324859 A1 | 12/2013 | Park et al. |
| 2014/0323824 A1 | 10/2014 | Addison et al. |
| 2015/0119578 A1 | 4/2015 | Vogt et al. |
| 2016/0128582 A1 | 5/2016 | Chod et al. |
| 2016/0198963 A1 | 7/2016 | Addison et al. |
| 2016/0220128 A1* | 8/2016 | Den Brinker ........ A61B 5/7203 |
| 2016/0287110 A1* | 10/2016 | Morris ............... A61B 5/02438 |
| 2018/0177413 A1* | 6/2018 | Kwon .................. A61B 5/742 |
| 2019/0076032 A1* | 3/2019 | Park .................. A61B 5/02438 |
| 2020/0008693 A1 | 1/2020 | Mukkamala et al. |
| 2021/0298618 A1* | 9/2021 | Mukkamala ....... A61B 5/02225 |

FOREIGN PATENT DOCUMENTS

| | | | |
|---|---|---|---|
| KR | 10-2006-0081178 A | 7/2006 | |
| KR | 10-2012-0058243 A | 6/2012 | |
| KR | 10-1577343 B1 | 12/2015 | |
| WO | 2005092178 A1 | 10/2005 | |
| WO | WO-2005092178 A1 * | 10/2005 | ......... A61B 5/02007 |
| WO | 2017152098 A1 | 9/2017 | |

OTHER PUBLICATIONS

Communication dated Jun. 9, 2020, issued by the European Patent Office in counterpart European Application No. 20155596.8.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2019-0014554, filed on Feb. 7, 2019, in the Korean Intellectual Property Office, the entire disclosure of which is incorporated herein by reference for all purposes.

BACKGROUND

1. Field

Example embodiments of the present disclosure relate generally to an apparatus and a method for estimating bio-information, and more particularly to technology for estimating blood pressure without using a cuff.

2. Description of the Related Art

Generally, methods of non-invasively measuring blood pressure without damaging a human body include a method to measure blood pressure by measuring a cuff-based pressure and a method to estimate blood pressure by measuring pulse waves without the use of a cuff.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of estimating blood pressure by calculating a Pulse Transit Time (PTT), and a method using Pulse Wave Analysis (PWA) for estimating blood pressure by analyzing a pulse wave shape.

SUMMARY

According to an aspect of the disclosure, there is provided an apparatus for estimating bio-information, the apparatus comprising: a sensor configured to measure a pulse wave signal from an object and contact pressure of the object; and a processor configured to: obtain an oscillometric envelope based on an amplitude of the pulse wave signal and the contact pressure, and estimate bio-information based on a center of mass of a phase of contact pressure of the obtained oscillometric envelope.

The sensor may comprise: a pulse wave sensor comprising: a light source configured to emit light onto the object, and a detector configured to detect the light reflected from the object; and a contact pressure sensor comprising: a force sensor configured to measure a contact force of the object, and an area sensor configured to measure a contact area of the object.

The processor may be further configured to determine a phase corresponding to an amplitude value, which is a predetermined percentage of a maximum amplitude value of the pulse wave signal in the oscillometric envelope, as the phase of contact pressure.

The processor may be further configured to: obtain the maximum amplitude value as a first feature, the phase of contact pressure as a second feature, and a contact pressure value corresponding to the center of mass as a third feature, and estimate the bio-information by combining the first feature, the second feature, and the third feature.

The processor may be further configured to assign a weight to each of the first feature, the second feature, and the third feature, and combines the first feature, the second feature, and the third feature.

The weight assigned to each of the first feature, the second feature, and the third feature may be a preset fixed value or a value adjusted based on any one or any combination of user characteristics and types of the bio-information.

The processor may be further configured to: extract a direct current (DC) component of the pulse wave signal, and obtain a fourth feature based on a graph of the extracted DC component and the contact pressure.

The processor may be further configured to: perform curve fitting for the graph by using a fitting model, and obtain a coefficient of the fitting model, which is determined as a result of the curve fitting, as the fourth feature.

The processor may be further configured to obtain any one or any combination of a maximum slope value, a contact pressure value at a maximum slope point, and a maximum amplitude value as the fourth feature from the graph.

The apparatus may further comprise an output interface configured to output guide information on the contact pressure between the object and the sensor based on a request for estimating the bio-information.

The guide information may comprise information for inducing a user to gradually increase the contact pressure or based on a determination that the contact pressure is greater than or equal to a predetermined threshold value, information for inducing the user to gradually decrease the contact pressure.

The processor may be further configured to: determine a contact state between the object and the sensor based on the contact pressure, and based on determining that the contact state of the object is abnormal, t guide a user to change the contact pressure.

The bio-information may comprise any one or any combination of blood pressure, vascular age, arterial stiffness, aortic pressure waveform, vascular compliance, stress index, or degree of fatigue.

According to another aspect of the disclosure, there is provided a method of estimating bio-information, the method comprising: obtaining, by a sensor, a pulse wave signal from an object and contact pressure of the object; obtaining an oscillometric envelope based on an amplitude of the pulse wave signal and the contact pressure; and estimating bio-information based on a center of mass of a phase of contact pressure of the obtained oscillometric envelope.

The estimating of the bio-information may comprise determining a phase corresponding to an amplitude value, which is a predetermined percentage of a maximum amplitude value of the pulse wave signal in the oscillometric envelope, as the phase of contact pressure.

The estimating of the bio-information may comprise obtaining the maximum amplitude value as a first feature, the phase of contact pressure as a second feature, and a contact pressure value corresponding to the center of mass as a third feature, and estimating the bio-information by combining the obtained first feature, the second feature, and the third feature.

The estimating of the bio-information may comprise assigning a weight to each of the first feature, the second feature, and the third feature, and combining the first feature, the second feature, and the third feature.

The estimating of the bio-information may further comprise extracting a direct current DC component of the pulse wave signal, and obtaining a fourth feature based on a graph of the extracted DC component and the contact pressure.

The obtaining of the fourth feature may comprise performing curve fitting for the graph by using a fitting model, and obtaining a coefficient of the fitting model, which is determined as a result of the curve fitting, as the fourth feature.

The obtaining of the fourth feature may comprise obtaining at least one of a maximum slope value, a contact pressure value at a maximum slope point, and a maximum amplitude value as the fourth feature from the graph.

The method may further comprise outputting guide information on the contact pressure between the object and the sensor based on a request for estimating the bio-information.

The method may further comprise determining a contact state between the object and the sensor based on the contact pressure; and based on determining that the contact state of the object is abnormal, guiding a user to change the contact pressure.

According to another aspect of the disclosure, there is provided an apparatus for estimating bio-information, the apparatus comprising: a sensor configured to measure a pulse wave signal from an object and contact pressure of the object; and a processor configured to: obtain one or more features based on a relationship between a direct current (DC) component of the pulse wave signal and the contact pressure, and estimate bio-information based on the obtained one or more features.

The processor may be further configured to extract the DC component from the pulse wave signal using a low-pass filter.

The processor may be further configured to: generate a graph based the contact pressure and the DC component by plotting a DC component value with respect to a contact pressure value at each measurement time, and obtain the one or more features based on the generated graph.

The processor may be further configured to: perform curve fitting for the graph using a fitting model, and obtain a coefficient of the fitting model, which is determined as a result of the curve fitting, as the one or more features.

The processor may be configured to obtain any one or any combination of a maximum slope value, a contact pressure value at a maximum slope point, or a maximum amplitude value as the one or more features from the graph.

According to another aspect of the disclosure, there is provided an apparatus for estimating bio-information, the apparatus comprising: a memory storing one or more instructions; and a processor configured to execute the one or more instructions to: obtain a pulse wave signal representing a vital function of a user detected by a sensor; obtain contact pressure values based on contact pressure applied by the user to the sensor in an increasing or decreasing manner, and estimate the bio-information based on the pulse wave signal and the contact pressure values.

The processor may be further configured to: obtain an oscillometric envelope based on an amplitude of the pulse wave signal and the contact pressure values, and estimate the bio-information based on a center of mass of a phase of contact pressure of the obtained oscillometric envelope.

The processor may be further configured to: obtain one or more features based on a relationship between a DC component of the pulse wave signal and the contact pressure values, and estimate the bio-information based on the obtained one or more features.

According to another aspect of the disclosure, there is provided a method for estimating bio-information, the method comprising: obtaining a pulse wave signal representing a vital function of a user detected by a sensor; obtaining contact pressure values based on contact pressure applied by the user to the sensor in an increasing or decreasing manner, and estimating the bio-information based on the pulse wave signal and the contact pressure values.

The estimating the bio-information may further comprise: obtaining an oscillometric envelope based on an amplitude of the pulse wave signal and the contact pressure values, and estimating the bio-information based on a center of mass of a phase of contact pressure of the obtained oscillometric envelope.

The estimating the bio-information may further comprise: obtaining one or more features based on a relationship between a DC component of the pulse wave signal and the contact pressure values, and estimating the bio-information based on the obtained one or more features.

BRIEF DESCRIPTION OF THE DRAWINGS

The above and/or other aspects will become apparent and more readily appreciated from the following description of example embodiments, taken in conjunction with the accompanying drawings in which.

DETAILED DESCRIPTION

Figure 1A:
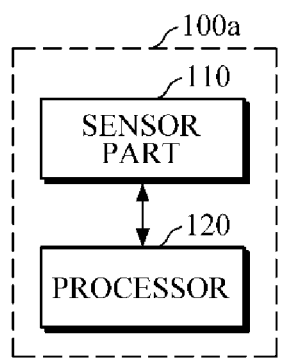
FIGS. 1A and 1B are block diagrams illustrating an apparatus for estimating bio-information according to example embodiments.

Details of example embodiments are included in the following detailed description and drawings. Advantages and features of the example embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Also, the singular forms are intended to include the plural forms as well, unless the context clearly indicates otherwise. In the specification, unless explicitly described to the contrary, the word "comprise" and variations, such as "comprise" or "comprising" will be understood to imply the inclusion of stated elements but not the exclusion of any other elements. Terms, such as 'part' and 'module' denote units that process at least one function or operation and they may be implemented by using hardware, software, or a combination thereof.

Hereinafter, example embodiments of an apparatus and method for estimating bio-information will be described in detail with reference to the accompanying drawings.

Figure 1B:
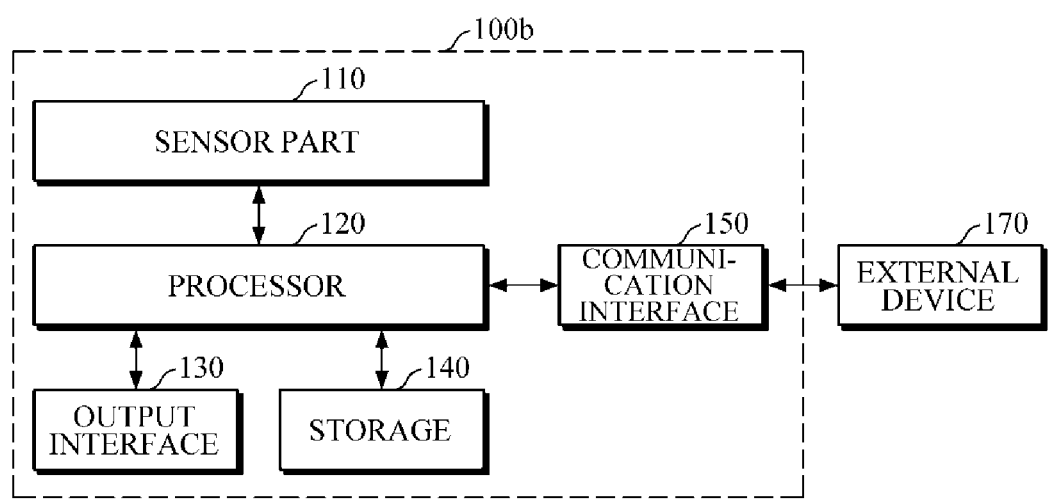

FIGS. 1A and 1B are block diagrams illustrating an apparatus for estimating bio-information according to example embodiments.

According to the example embodiments of, the bio-information estimating apparatuses 100a and 100b may be embedded in a medical device used in a specialized medical institution, in a smartwatch worn on the wrist, various types of wearable devices such as a smart band type wearable device, a headphone type wearable device, a headband type wearable device, and the like, or in a mobile device such as a smartphone, a tablet PC, and the like, but are not limited thereto.

Referring to FIGS. 1A and 1B, the bio-information estimating apparatuses 100a and 100b includes a sensor part 110 and a processor 120.

The sensor part 110 may include a pulse wave sensor which measures a photoplethysmography (PPG) signal from an object. The pulse wave sensor may include a light source which emits light onto the object; and a detector which detects scattered or reflected light when light emitted by the light source is scattered or reflected from body tissue of the object such as the surface of skin or blood vessels. According to an example embodiment, the object is body part of a person or a user of the bio-information estimating apparatus.

The light source may include a light emitting diode (LED), a laser diode (LD), a fluorescent body, and the like, but is not limited thereto. The detector may include a photo diode, a photo transistor (PTr), an image sensor (e.g., CMOS image sensor), or the like, but is not limited thereto. According to an example embodiment, the detector may include one or more pixels, each of which may include the photo diode, the photo transistor (PTr), the image sensor (e.g., CMOS image sensor), or the like, but is not limited thereto. The pulse wave sensor may be formed of an array of a plurality of light sources and/or an array of a plurality of detectors to measure two or more pulse wave signals. In this case, the plurality of light sources may emit light of the same wavelength or light of different wavelengths. The plurality of detectors may be positioned at different distances from the light sources.

The sensor part 110 may include a contact pressure sensor. When an object, which is in contact with the sensor part 110, applies force to the sensor part 110 to measure a pulse wave signal, the contact pressure sensor may measure a contact force and a contact area. In this case, the contact pressure sensor may include a force sensor for measuring a contact force applied by the object to the sensor part 110, and an area sensor for measuring a contact area between the object and the sensor part 110 as the contact force applied by the object is changed.

The processor 120 may process various operations of estimating bio-information. For example, the processor 120 may control the sensor part 110 upon receiving a request for estimating bio-information from a user. According to another example embodiment, the processor 120 may control the sensor part 110 if a predetermined criteria for estimating bio-information are satisfied. The processor 120 may be electrically connected to the sensor part 110, and may receive the pulse wave signal and information on contact pressure from the sensor part 110. In this case, the information on contact pressure may be a contact force and a contact area, or a contact pressure value itself.

Further, the processor 120 may estimate bio-information based on the pulse wave signal and the information on contact pressure. For example, upon receiving the contact force and the contact area, the processor 120 may obtain contact pressure by dividing the contact force by the contact area. In this case, the bio-information may include heart rate, blood pressure, vascular age, arterial stiffness, aortic pressure waveform, vascular compliance, stress index, and degree of fatigue, skin elasticity, skin age, and the like, but is not limited thereto. Hereinafter, description will be given, if necessary, using blood pressure as an example for convenience of explanation.

The processor 120 may obtain features for estimating bio-information based on the pulse wave signal and the contact pressure, and may estimate bio-information based on the obtained features. For example, the processor 120 may obtain an oscillometric envelope based on the pulse wave signal and the contact pressure, and may obtain the features by using the obtained oscillometric envelope. In another example, the processor 120 may obtain the features for estimating bio-information by using a relationship between a DC component of the pulse wave signal and the contact pressure. In an example, the DC component of the pulse wave signal the mean amplitude of the pulse wave signal.

Referring to FIG. 1B, the bio-information estimating apparatus 100b may further include an output interface 130, a storage 140, and a communication interface 150.

The output interface 130 may output results processed by the sensor part 110 and the processor 120. For example, the output interface 130 may visually output an estimated bio-information value and/or guide information through a display module, or may non-visually output the information by voice, vibrations, tactile sensation, and the like using a speaker module, a haptic module, and the like. The output interface 130 may divide a display area into two or more areas, in which the output interface 130 may output a pulse wave signal used for estimating bio-information, a contact force, a contact area, and the like in the form of various graphs and the like in a first area; and along with the information, the output interface 130 may output an estimated bio-information value in a second area. In this case, if the estimated bio-information value falls outside a normal range, the output interface 130 may output warning information in various manners, such as highlighting an abnormal value in red and the like, displaying the abnormal value along with a normal range, outputting a voice warning message, adjusting a vibration intensity, and the like.

The storage 140 may store processing results of the sensor part 110 and the processor 120. Further, the storage 140 may store a variety of reference information required for estimating bio-information. For example, the reference information may include user characteristic information such as a user's age, sex, health condition, and the like. In addition, the reference information may include a variety of information such as a bio-information estimation model, criteria for estimating bio-information, a reference contact pressure value, a reference feature value, and the like, but is not limited thereto.

In this case, the storage 140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 150 may communicate with an external device 170 by using wired or wireless communication techniques under the control of the processor 120, and may transmit and receive various data to and from the external device 170. For example, the communication interface 150 may transmit a bio-information estimation result to the external device 170, and may receive, from the external device 170, a variety of reference information required for estimating bio-information. In this case, the external device 170 may include a cuff-type blood pressure measuring device and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

According to another example embodiment, one or more of the sensor part 110, the processor 120, the output interface 130, the storage 140, and the communication interface 150 may be external to the bio-information estimating apparatus 100b.

Figure 2:
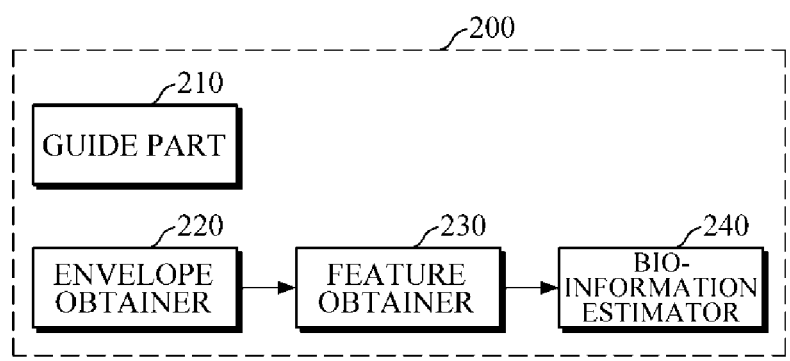
FIG. 2 is a block diagram illustrating a configuration of a processor of the apparatus for estimating bio-information according to the example embodiments of FIGS. 1A and 1B.
Figure 3A:
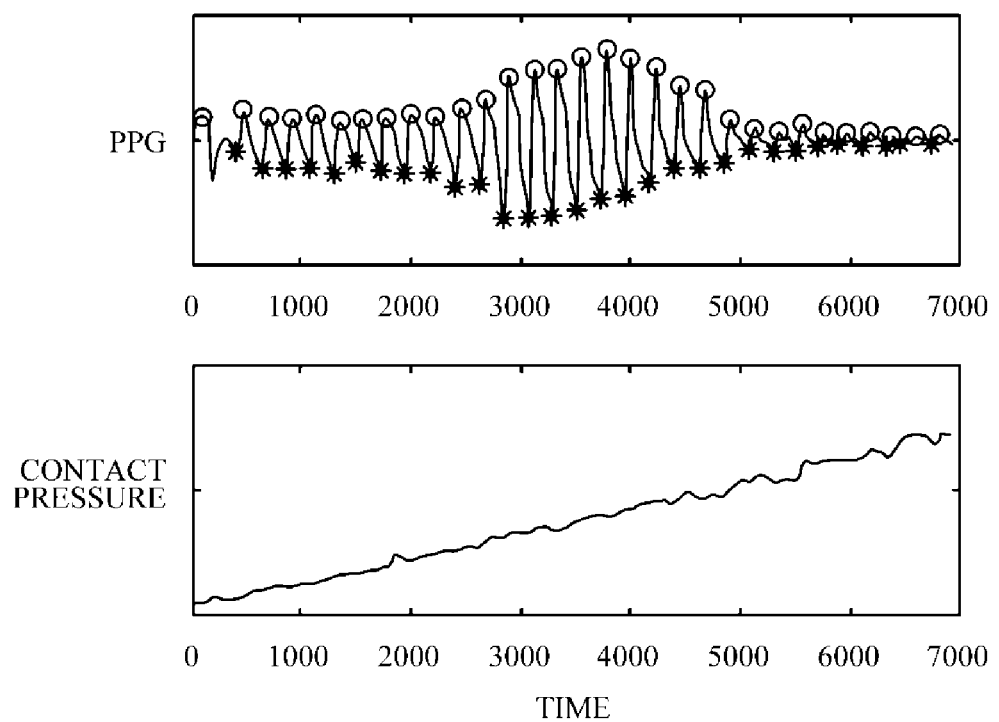
FIGS. 3A, 3B, and 3C are diagrams explaining an example of obtaining features according to an example embodiment.
Figure 3B:
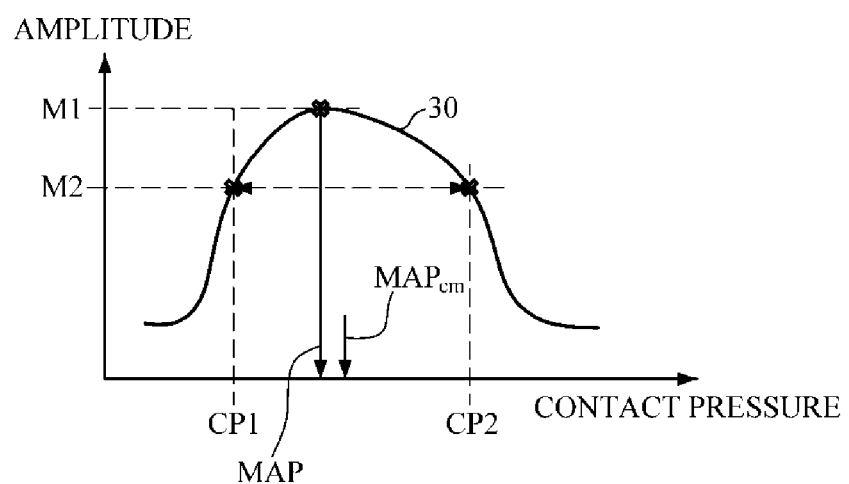
Figure 3C:
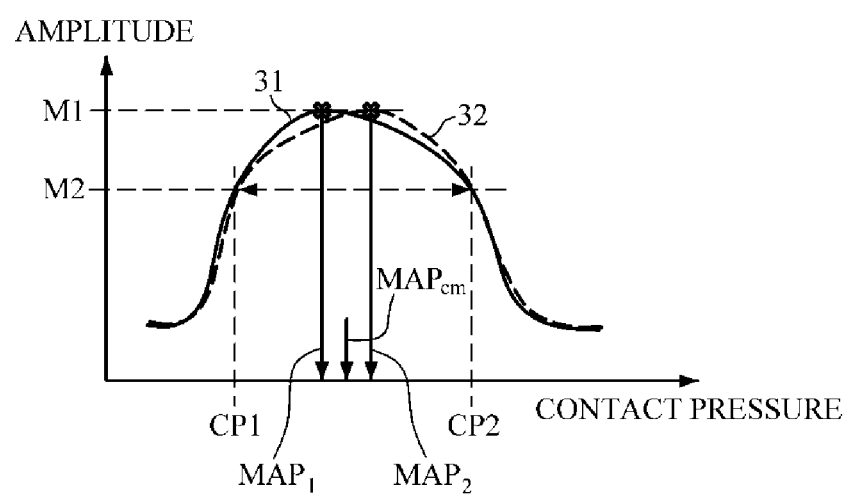

FIG. 2 is a block diagram illustrating a configuration of a processor of the apparatus for estimating bio-information according to the example embodiments of FIGS. 1A and 1B; and FIGS. 3A to 3C are diagrams explaining an example of obtaining features according to an example embodiment.

Referring to FIG. 2, the processor 200 according to an example embodiment includes a guide part 210, an envelope obtainer 220, a feature obtainer 230, and a bio-information estimator 240.

According to an example embodiment, based on receiving a request for estimating bio-information, the guide part 210 may refer to the reference information of the storage 140 to generate guide information on contact pressure to be applied by an object to the sensor part 110 for measuring a pulse wave signal (hereinafter referred to as "reference contact pressure"). For example, in order to induce a change in amplitude of the pulse wave signal, the guide information may include information for inducing a gradual increase in contact pressure while an object is in contact with the sensor part 110. On the other hand, the guide information may include information for inducing a gradual decrease in contact pressure when the contact pressure greater than or equal to a predetermined threshold value is applied.

Further, upon obtaining real-time contact pressure applied by the object to the sensor part 110 (hereinafter referred to as "actual contact pressure"), the guide part 220 may generate guide information based on the obtained actual contact pressure to guide a user to adjust contact pressure. In this case, the processor 120 may determine a contact state of the object based on the actual contact pressure, and if the contact state is not normal, the guide part 220 may generate guide information for adjusting the contact pressure. For example, if a difference between an actual contact pressure and a reference contact pressure at a specific time is greater than or equal to a predetermined threshold value, the processor 120 may determine that the contact state is abnormal.

The envelope obtainer 220 may obtain an oscillometric envelope based on the pulse wave signal and the contact pressure.

FIG. 3A is a diagram illustrating a PPG signal and contact pressure measured from an object by the sensor part 110. As illustrated in FIG. 3A, when a user gradually increases contact pressure while an object is in contact with the sensor part 110, the amplitude of the pulse wave signal also gradually increases for a predetermined period of time. The envelope obtainer 220 may normalize the pulse wave signal, and may extract a peak-to-peak point of the pulse wave signal waveform by subtracting a negative (−) amplitude value from a positive (+) amplitude value of a waveform envelope at each measurement time of the pulse wave signal, and may obtain the oscillometric envelope, which represents contact pressure versus pulse wave, by plotting the peak-to-peak point with respect to the contact pressure value at each measurement time.

The feature obtainer 230 may obtain features for estimating bio-information by using the obtained oscillometric envelope. In the oscillometry-based method for estimating blood pressure, blood pressure may be generally estimated by obtaining a contact pressure value (MAP) at a maximum peak point as a feature related to mean arterial pressure; and obtaining contact pressure values at the right and left points, which are symmetrically distant from the contact pressure value at the maximum peak point and which have a preset peak ratio within a range from 0.5 to 0.7, as features related to systolic blood pressure (SBP) and diastolic blood pressure (DBP).

FIG. 3B is a diagram illustrating an example of an oscillometric envelope. Referring to FIG. 3B, the feature obtainer 230 may obtain, from an oscillometric envelope 30, information items related to the center of mass of a predetermined phase of contact pressure values CP1 and CP2 as features for estimating blood pressure.

For example, the feature obtainer 230 may obtain a maximum amplitude value M1 of the oscillometric envelope 30 as a first feature. Further, the feature obtainer 230 may obtain, as a second feature, the phase of the contact pressure values CP1 and CP2 corresponding to an amplitude value M2 which is a predetermined percentage of the maximum amplitude value in the oscillometric envelope 30. In this case, the predetermined percentage may be set to various numbers based on a type of bio-information, user characteristics, and the like, and may be set to, for example, any number greater than or equal to 90%. In this case, the second feature may include any one or a combination of two or more of a first contact pressure value CP1, a second contact pressure value CP2, a difference between the first contact pressure value CP1 and the second contact pressure value CP2, an area of a region between the first contact pressure value CP1 and the second contact pressure value CP2 of the oscillometric envelope 30. In addition, the feature obtainer 230 may obtain, as a third feature, a contact pressure value $MAP_{cm}$ corresponding to a center of mass of the phase of the contact pressure values CP1 and CP2 of the oscillometric envelope 30, that is, the center of mass of a region between the first contact pressure value CP1 and the second contact pressure value CP2 of the oscillometric envelope 30. In this case, the center of mass may be calculated using a weighted mean of the region. However, the feature is not limited thereto, and various other features may also be obtained.

FIG. 3C is a diagram explaining an example, in which, a contact pressure value corresponding to a maximum amplitude value is changed. For example, as illustrated in FIG. 3C, it is assumed that the maximum amplitude value M1, and the amplitude value M2 corresponding to a predetermined percentage (e.g., 90%) of the maximum amplitude value M1, of two oscillometric envelopes 31 and 32 are the same but symmetrical due to motion noise and the like. In this case, a contact pressure value $MAP_1$, corresponding to the maximum amplitude value of the first oscillometric envelope 31, and a contact pressure value $MAP_2$, corresponding to the maximum amplitude value of the second oscillometric envelope 32, are different from each other, such that the accuracy of estimating blood pressure may be degraded. By contrast, in the example embodiment, a contact pressure value $MAP_{cm}$, corresponding to the center of mass of the region of the contact pressure values CP1 and CP2 corresponding to the maximum value M2 which is a predetermined percentage of the maximum amplitude value M1, occurs at the same point, thereby obtaining robust features for estimating blood pressure and improving accuracy of estimating blood pressure.

The bio-information estimator 240 may estimate bio-information by using a bio-information estimation model for linearly of non-linearly combining the features obtained by the feature obtainer 230. In this case, the bio-information estimation model may be defined as various linear or non-linear combination functions, such as addition, subtraction, division, multiplication, logarithmic value, regression equation, and the like, with no specific limitation. For example, the following Equation 1 represents a function for combining the first feature, the second feature, and the third feature.

$$y = af_1 + bf_2 + cf_3 \quad \text{[Equation 1]}$$

Herein, y denotes bio-information to be obtained; $f_1$ denotes the first feature; $f_2$ denotes the second feature; $f_3$ denotes the third feature; and a, b, and c denote weights assigned to each of the features, and may be fixed values obtained as a result of preprocessing or values adjusted in consideration of bio-information to be obtained and user characteristics.

Figure 4A:
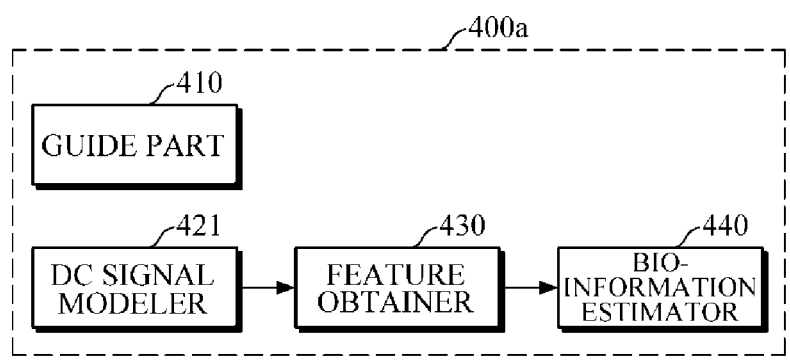
FIGS. 4A and 4B are diagrams illustrating a configuration of a processor of the apparatus for estimating bio-information according to another example embodiment.
Figure 4B:
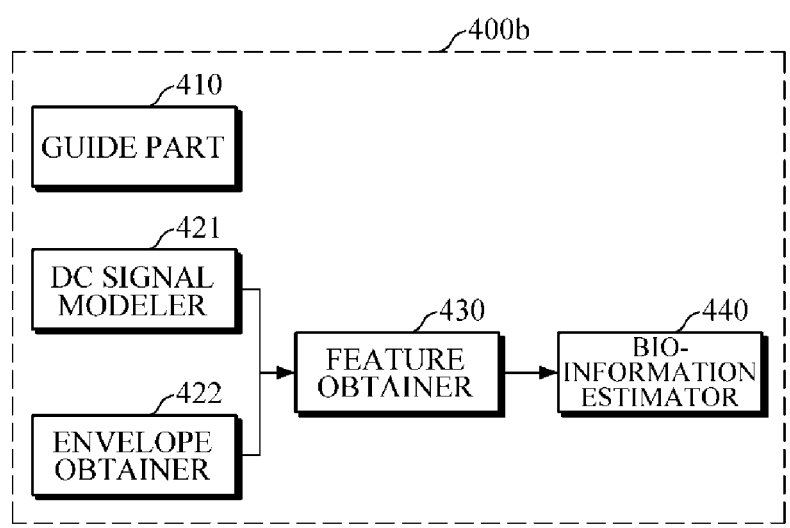

FIGS. 4A and 4B are diagrams illustrating a configuration of a processor of the apparatus for estimating bio-information according to another example embodiment; and FIGS. 5A to 5D are diagrams explaining an example of obtaining features by modeling a DC signal.

According to an example embodiment illustrated in FIG. 4A, the processor 400a includes a guide part 410, a DC signal modeler 421, a feature obtainer 430, and a bio-information estimator 240.

According to an example embodiment, based on a request for estimating bio-information, the guide part 410 provides guide information on a reference contract pressure. Once the sensor part 110 obtains an actual contact pressure from an object actually being in contact with the sensor part 110, the guide part 410 may determine a contact state based on the obtained actual contact pressure. Further, based on the determination on the contact state, the guide part 410 may generate information for guiding a user to adjust contact pressure of the object.

The DC signal modeler 421 may perform modeling on a DC signal of the pulse wave signal measured by the sensor part 110. The DC signal modeler 421 may extract a DC component of the pulse wave signal by using a low-pass filter (LPF). In addition, the DC signal modeler 421 may generate a contact pressure versus DC component graph, which is similar to a curve of a blood vessel volume change, based on the extracted DC component of the pulse wave signal and the contact pressure.

Figure 5A:
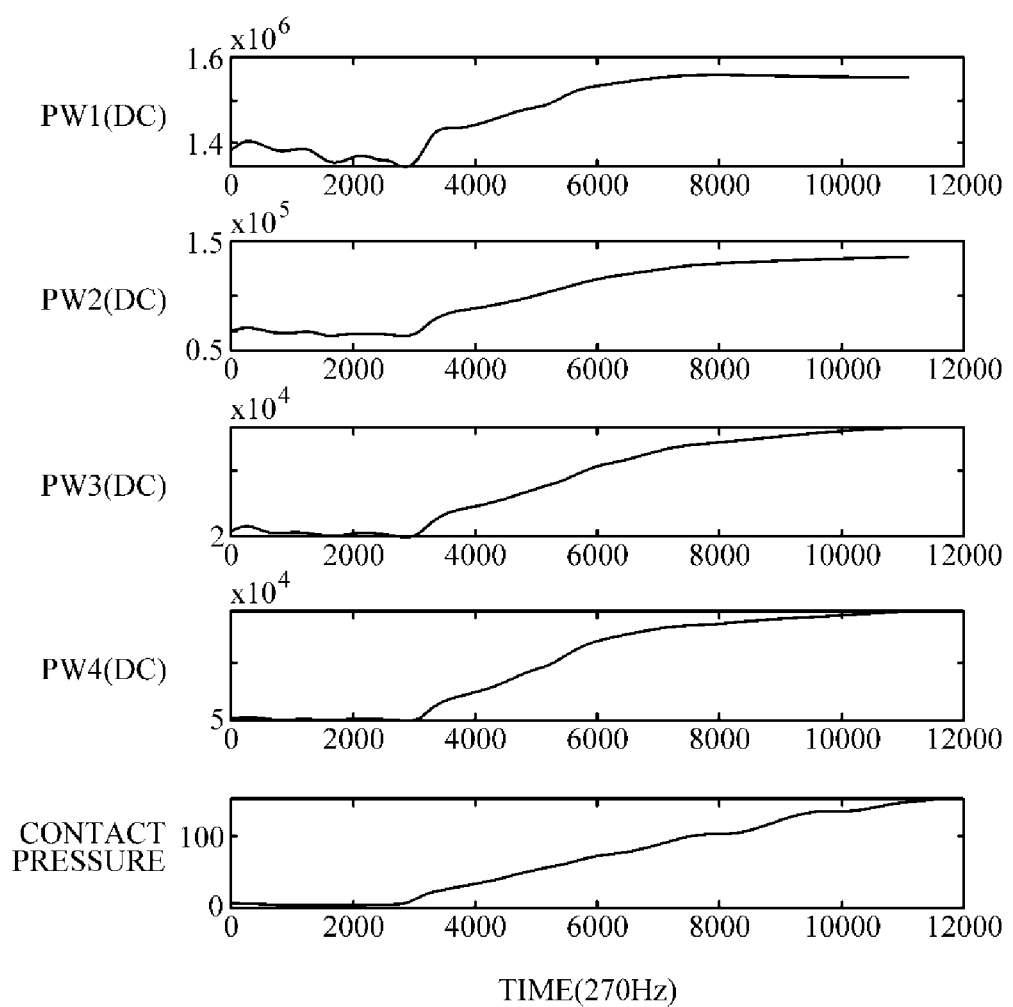
FIGS. 5A, 5B, 5C, and 5D are diagrams explaining an example of obtaining features according to another example embodiment.

For example, FIG. 5A illustrates a relationship between DC components of the pulse wave signal and contact pressure. As illustrated in FIG. 5A, as the contact pressure gradually increases, the DC components of the pulse wave signal also gradually increase.

Figure 5B:
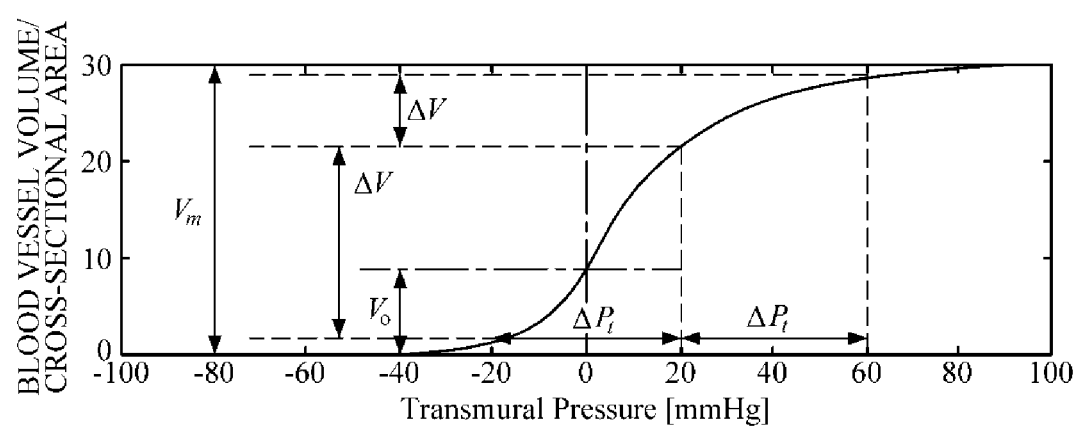

FIG. 5B illustrates a graph showing a relationship between transmural pressure and blood vessel volume of blood vessels. The transmural pressure may be defined as a value obtained by subtracting external pressure from internal pressure exerted on the blood vessels. Referring to FIG. 5B, it can be generally seen that as the transmural pressure increases, the blood vessel volume increases sharply and then an increment in the blood vessel volume gradually decreases.

Figure 5C:
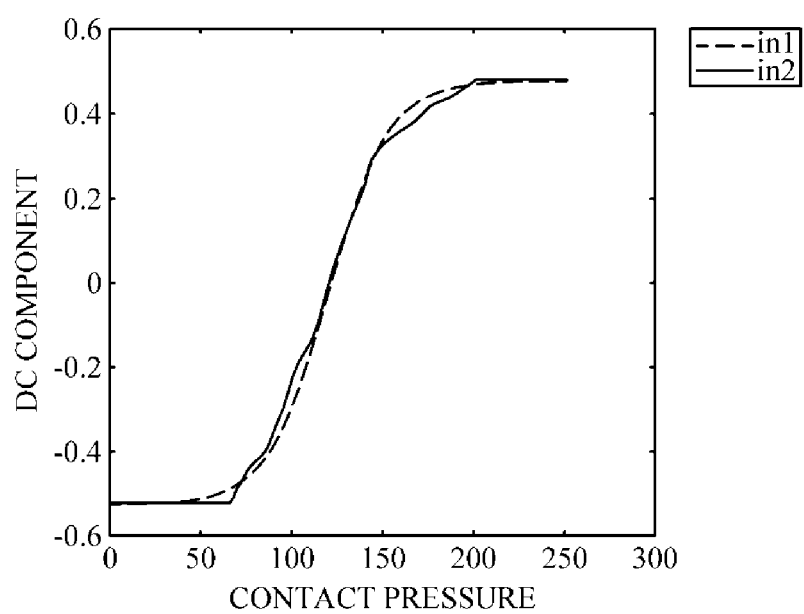

FIG. 5C is a diagram illustrating a contact pressure versus DC component graph. The contact pressure versus DC component graph shows a pattern similar to transmural pressure versus blood vessel volume change. The DC signal modeler 421 may generate a first graph (in2), which represents contact pressure versus DC component, by plotting the DC component values of the pulse wave signal with respect to the contact pressure value at each measurement time. Further, the DC signal modeler 421 may generate a second graph (in1) by performing curve fitting for the first graph (in2) using a fitting model.

The following Equation 2 is an example of a fitting model, and Equation 3 is an example of basic functions of the fitting model.

$$y = F(X) \quad \text{[Equation 2]}$$

$$y = c_1 f(c_2(x + c_3)) + c_4$$

$$\mathrm{erf}\left(\frac{\sqrt{\pi}}{2} x\right) \quad \text{[Equation 3]}$$

$$\tanh(x)$$

$$\frac{x}{\sqrt{1 + x^2}}$$

$$\frac{2}{\pi} gd\left(\frac{\pi}{2} x\right)$$

$$\frac{2}{\pi} \arctan\left(\frac{\pi}{2} x\right)$$

$$\frac{x}{1 + |x|}$$

The feature obtainer 430 may obtain features for estimating bio-information by using the graph, for which curve fitting is performed.

Figure 5D:
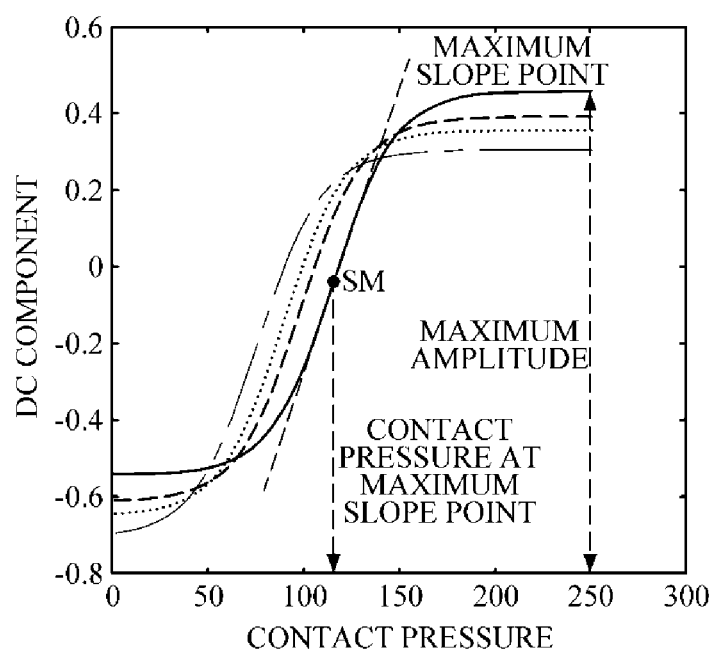

For example, the feature obtainer 430 may obtain, as features, $c_1$, $c_2$, $c_3$, and $c_4$ for optimizing the fitting model in Equation 2 above. Further, as illustrated in FIG. 5D, the feature obtainer 430 may obtain, as additional features, a maximum slope value, a contact pressure value at a maximum slope point SM, a maximum amplitude value, and the like.

The bio-information estimator 440 may estimate bio-information by using a bio-information estimation model for linearly of non-linearly combining the features obtained by the feature obtainer 430. In this case, the bio-information estimation model may be defined as various linear or non-linear combination functions, such as addition, subtraction, division, multiplication, logarithmic value, regression equation, and the like, with no specific limitation.

Referring to FIG. 4B, the processor 400b according to another example embodiment may further include the guide part 410, the DC signal modeler 421, the envelope obtainer 422, the feature obtainer 430, and the bio-information estimator 440, each of which is described in detail above, such that redundant description thereof will be omitted.

In the example embodiment, by using both the oscillometric envelope and the contact pressure versus DC component graph, the processor 400b may obtain, as features, a contact pressure value corresponding to a maximum amplitude value, a contact pressure phase corresponding to a predetermined percentage of the maximum amplitude value, a contact pressure value corresponding to a center of mass of the contact pressure phase, coefficients of a curve fitting model, a maximum slope value, a contact pressure value at a maximum slope point, a maximum amplitude value, and the like, and may estimate bio-information by linearly of non-linearly combining all or some of the obtained features appropriately.

Figure 6:
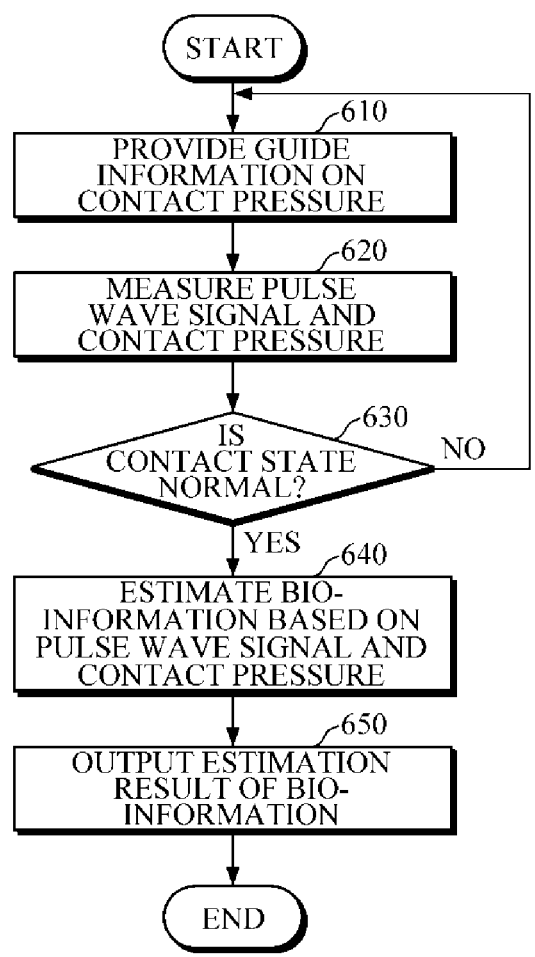
FIG. 6 is a flowchart illustrating a method of estimating bio-information according to an example embodiment.

FIG. 6 is a flowchart illustrating a method of estimating bio-information according to an example embodiment.

The bio-information estimating method of FIG. 6 may be performed by the bio-information estimating apparatuses 100a and 100b, which are described above in detail, such that the following description will be briefly made.

According to an example embodiment, based on receiving a request for estimating bio-information, the bio-information estimating apparatuses 100a and 100b may provide guide information on a reference contact pressure to be applied by a user's object to a sensor part for a predetermined period of time while a pulse wave signal is measured in operation 610. In this case, the request for estimating bio-information may be received from a user or an external device. Alternatively, for continuous measurements, it may be determined automatically at predetermined intervals that the request for estimating bio-information is received. According to another example embodiment, operation 610 may be omitted if necessary.

In operation 620, the bio-information estimating apparatuses 100a and 100b may measure a pulse wave signal and contact pressure for a predetermined period of time while the user changes the contact pressure when the object is in contact with the sensor part. In this case, the user may change the contact pressure by pressing the sensor part with a finger with gradually increasing force or by pressing the sensor part with gradually decreasing force when the user contacting the sensor part with the finger applies pressure equal to or greater than a predetermined threshold.

In operation 630, the bio-information estimating apparatuses 100a and 100b may determine a contact state based on the actual contact pressure measured in operation 620. For example, if an actual contact pressure at a specific time falls outside a threshold value compared to the reference contact pressure provided in operation 610, the bio-information estimating apparatuses 100a and 100b may determine that a contact state is abnormal, and may return to operation 610 of guiding contact pressure to provide guide information for adjusting contact pressure. According to an example embodiment, operation 630 may be omitted if necessary.

In operation 640, the bio-information estimating apparatuses 100a and 100b may estimate bio-information based on the pulse wave signal and the contact pressure.

Figure 7:
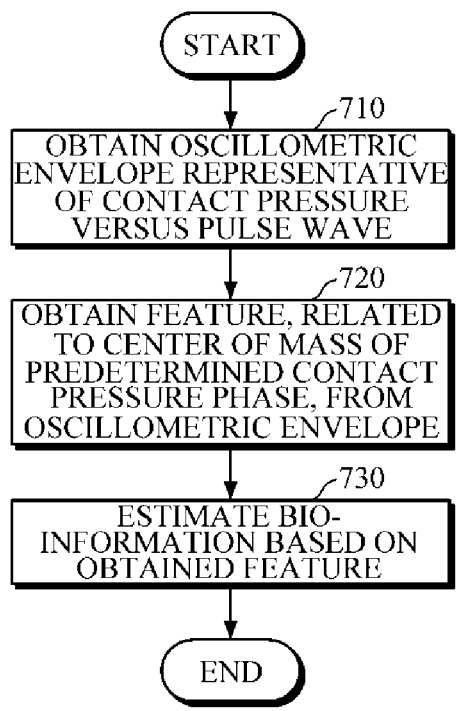
FIGS. 7 and 8 are diagrams illustrating examples of estimating bio-information of FIG. 6.
Figure 8:
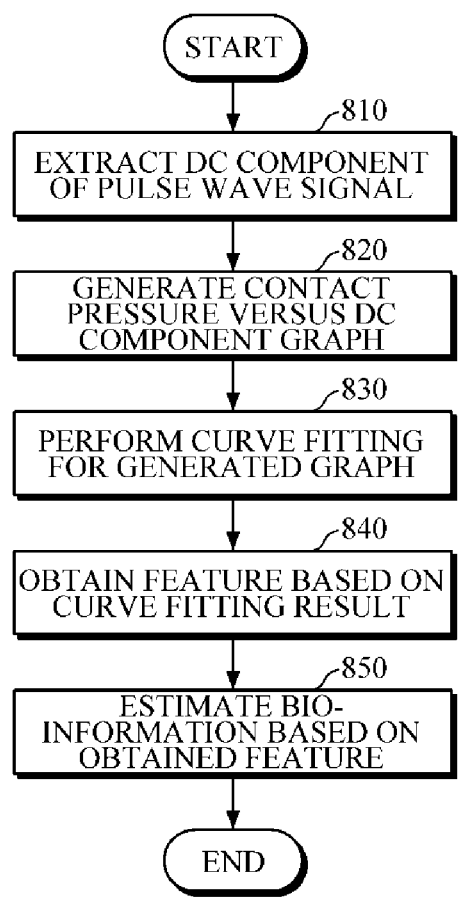

FIGS. 7 and 8 are diagrams illustrating examples of estimating bio-information in 640.

According to an example embodiment illustrated in FIG. 7, the bio-information estimating apparatuses 100a and 100b may obtain an oscillometric envelope in operation 710 based on the pulse wave signal and the contact pressure measured in 620.

In operation 720, the bio-information estimating apparatuses 100a and 100b may obtain features, related to the center of mass of a predetermined contact pressure phase, from the oscillometric envelope. For example, the bio-information estimating apparatuses 100a and 100b may obtain, as features, a contact pressure value corresponding to a maximum amplitude value, a contact pressure phase corresponding to a predetermined percentage of the maximum amplitude value, a contact pressure value corresponding to the center of mass of the contact pressure phase, and the like from the oscillometric envelope.

In operation 730, the bio-information estimating apparatuses 100a and 100b may estimate bio-information by linearly or non-linearly combining the obtained features.

According to another example embodiment illustrated in FIG. 8, in operation 810, the bio-information estimating apparatuses 100a and 100b may extract a DC component of the pulse wave signal measured in 620. For example, the bio-information estimating apparatuses 100a and 100b may extract the DC component signal by passing the pulse wave signal through a low-pass filter (LPF).

In operation 820, Then, the bio-information estimating apparatuses 100a and 100b may generate a graph plotting contact pressure versus DC component by using the contact pressure measured in 620 and the pulse wave DC component extracted in operation 810.

In operation 830, by using a fitting model, the bio-information estimating apparatuses 100a and 100b may perform curve fitting in 830 for the contact pressure versus DC component graph generated in operation 820.

In operation 840, the bio-information estimating apparatuses 100a and 100b may obtain features for estimating bio-information based on a curve fitting result. For example, the bio-information estimating apparatuses 100a and 100b may obtain, as features, coefficients of the fitting model optimized as a result of the curve fitting. Further, the bio-information estimating apparatuses 100a and 100b may obtain, as additional features, a maximum slope value, a contact pressure value at a maximum slope point, a maximum amplitude value, and the like from the contact pressure versus DC component graph.

In operation 850, the bio-information estimating apparatuses 100a and 100b may estimate bio-information by linearly of non-linearly combining the obtained features in 850.

Referring back to FIG. 6, the bio-information estimating apparatuses 100a and 100b may output an estimation result of bio-information in 650. For example, the bio-information estimating apparatuses 100a and 100b may visually or non-visually output the estimation result of bio-information using a display module, a speaker module, a haptic module, and the like.

According to another example embodiment, an estimating bio-information apparatus may include a memory storing one or more instructions and a processor configured to execute the one or more instructions to obtain a pulse wave signal representing a vital function of a person detected by a sensor, obtain contact pressure values based on contact pressure applied by the user to the sensor in an increasing or decreasing manner and estimate the bio-information based on the pulse wave signal and the contact pressure values.

According to an example embodiment, the processor may further obtain an oscillometric envelope based on an amplitude of the pulse wave signal and the contact pressure values, and estimate the bio-information based on a center of mass of a phase of contact pressure of the obtained oscillometric envelope.

According to an example embodiment, the processor may further obtain one or more features based on a relationship between a DC component of the pulse wave signal and the contact pressure values, and estimate the bio-information based on the obtained one or more features.

Figure 9:
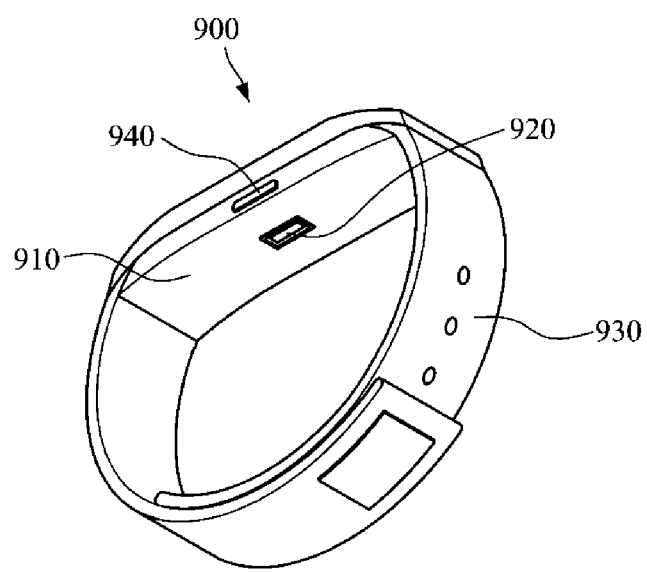
FIG. 9 is a diagram illustrating an example of a wearable device including the apparatus for estimating bio-information according to an example embodiment.

FIG. 9 is a diagram illustrating an example of a wearable device, to which the example embodiments of the aforementioned apparatuses 100a and 100b for estimating bio-information are applied.

Referring to FIG. 9, the wearable device 900 includes a main body 910 and a strap 930.

The strap 930 may be flexible, and may be connected to both ends of the main body 910 to be bent around a user's wrist or may be bent in a manner which allows the strap 930 to be detached from a user's wrist. Alternatively, the strap 930 may be formed as a band that is not detachable. In this case, air may be injected into the strap 930 or an airbag may be included in the strap 930, so that the strap 930 may have elasticity according to a change in pressure applied to the wrist, and the change in pressure of the wrist may be transmitted main body 910.

A battery, which supplies power to the wearable device 900, may be embedded in the main body 910 or the strap 930.

Further, a sensor part 920 is mounted on one side of the main body 910. The sensor part 920 may include an area sensor which comes into contact with the wrist to measure a contact area of the wrist; a pulse wave sensor which measures a pulse wave signal from blood vessel tissue of the wrist being in contact with the area sensor; and a force sensor which measures a contact force between the wrist and the area sensor. The pulse wave sensor may include c e light sources for emitting light onto the wrist; and a detector for detecting light reflected or scattered from the blood vessel tissue. In this case, each of the light sources may emit light of different wavelengths, and may be disposed at different distances from the detector.

When a use contact pressure between the wrist and the scars 920 for a predetermined period of time for estimating bio-information the sensor part 920 may measure the pulse wave signal, the contact force, and the contact area. For example, while wearing the main body 910, the user may change contact pressure between the wrist and the sensor part 920 by pressing a display, mounted on one surface of the main body 910, e.g., a surface opposite to the sensor part 920, with a finger of the other hand with gradually increasing force. Alternatively, while wearing the main body 910 on the wrist, the user may change a thickness of the wrist by making hand movements, e.g., slowly opening the hand after clenching the fist. In this case, the change in the thickness of the wrist leads to a change in tension of the strap wrapped around the wrist, thereby causing a change in contact pressure between the wrist and the sensor part 920.

In addition, the main body 910 may include a processor, which may estimate bio-information by using information such as the pulse wave signal, the contact force, the contact area, and the like, and may control various other functions of the wearable device 900.

The processor may control the sensor part 920 by generating a control signal in response to a user's request for estimating bio-information. The processor may obtain an oscillometric envelope based on the pulse wave signal and the contact pressure, and may obtain features, related to the center of mass of a predetermined contact pressure phase, by using the obtained oscillometric envelope. Alternatively, the processor may generate a graph of contact pressure versus DC component of the pulse wave signal, and may obtain features by using a result of curve fitting performed for the generated graph. Upon obtaining such various features, the processor may estimate bio-information by linearly of non-linearly combining the features using a bio-information estimating model.

According to an example embodiment, based on receiving the request for estimating bio-information from a user, the processor may provide guide information on contact pressure to the user through a display, so that the user may change contact pressure between the sensor part 920 and the object by applying pressure to the main body 910.

In this case, the display may be mounted on a front surface of the main body 910, and may visually output guide information on contact pressure and/or an estimation result of bio-information.

A storage may be mounted in the main body 910, and may store a variety of information processed by the processor, and a variety of reference information for estimating bio-information.

Further, the wearable device 900 may include a manipulator 940 which receives a control command of a user and transmits the received control command to the processor. The manipulator 940 may be mounted on a side surface of the main body 910, and may include a function for inputting a command for power on/off of the wearable device 900.

Moreover, the wearable device 900 may include a communication interface for transmitting and receiving various data to and from an external device, and various other modules for performing additional functions provided by the wearable device 900.

Figure 10:
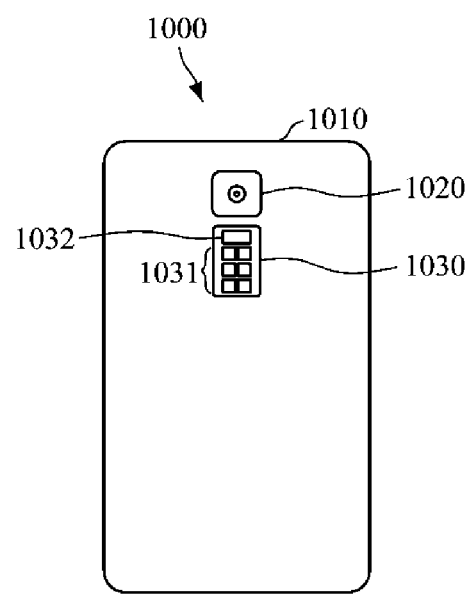
FIG. 10 is a diagram illustrating an example of a smart device including the apparatus for estimating bio-information according to an example embodiment.

FIG. 10 is a diagram illustrating a smart device, to which example embodiments of the apparatus for estimating bio-information are applied. In this case, the smart device may be a smartphone, a tablet PC, and the like.

Referring to FIG. 10, the smart device 1000 includes a main body 1010 and a sensor part 1030 mounted on one surface of the main body 1010. The sensor part 1030 may, include a pulse wave sensor, including one or more light sources 1031 and a detector 1032, a force sensor, and an area sensor. As illustrated in FIG. 10, the sensor part 1030 may be mounted on a rear surface of the main body 1010, but is not limited thereto, and may be configured in combination with a fingerprint sensor or a touch panel formed on the front surface of the main body 1010. In this case, the fingerprint sensor or a touch panel may perform a function of an area sensor, and the pulse wave sensor and the force sensor may be mounted at the bottom of the fingerprint sensor or a touch panel.

In addition, a display may be mounted on a front surface of the main body 1010. The display may visually display an estimation result of bio-information and the like. The display may include a touch panel, and may receive a variety of information input through the touch panel and transmit the received information to the processor.

Moreover, an image sensor 1020 may be mounted in the main body 1010. When a user's finger approaches the sensor part 1030 to measure a pulse wave signal, the image sensor 1020 may capture an image of the finger and may transmit the captured image to the processor. In this case, based on the image of the finger, the processor may identify a relative position of the finger with respect to an actual position of the sensor part 1030, and may provide the relative position of the finger to the user through the display, so that pulse wave signals may be measured with improved accuracy.

Various other modules for performing one or more of the example embodiments of the aforementioned apparatus for estimating bio-information may be mounted in the smart device 1000, and detailed description thereof will be omitted.

According to an example embodiment, the processor in any of FIGS. 1-10 may be a data processor implemented as hardware including a circuit having a physical structure for executing desired operations. For example, the desired operations may include code or instructions included in a program. For example, examples of the data processor implemented as hardware may include a microprocessor, a central processing unit, a processor core, a multi-core processor, a multiprocessor, an application-specific integrated circuit ASIC), a field programmable gate array (FPGA), and so forth.

One or more example embodiments can be realized as a computer-readable code written on a non-transitory computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the one or more example embodiments can be readily deduced by programmers in the technical field to which the disclosure pertains.

The inventive concepts have been described herein with regard to the example embodiments. However, it will be obvious to those skilled in the art that various changes and modifications can be made without changing technical conception and essential features. Thus, it is clear that the above-described example embodiments are illustrative in all aspects and are not intended to limit the disclosure.

What is claimed is:

1. An apparatus for estimating bio-information, the apparatus comprising:
a pulse wave sensor configured to measure a pulse wave signal from an object during a measurement period;
a contact pressure sensor configured to measure contact pressure of the object during the measurement period; and
a processor configured to:
extract a peak-to-peak amplitude of the pulse wave signal of each measurement time during the measurement period by subtracting an amplitude value of a negative (−) point from an amplitude value of a positive (+) point of a waveform envelope of the pulse wave signal corresponding to the each measurement time;
obtain an oscillometric envelop by plotting the extracted peak-to-peak amplitude of the pulse wave signal with respect to the contact pressure at the each measurement time;
determine a first contact pressure value and a second contact pressure value on the oscillometric envelope, each of the first contact pressure value and the second contact pressure value corresponding to a predetermined percentage of a maximum amplitude value of the oscillometric envelope;
obtain a third contact pressure value corresponding to a center of mass of a region between the first contact pressure value and the second contact pressure value on the oscillometric envelope based on a weighted mean of the region;
estimate the bio-information based on the third contact pressure value, and
output a notification in real-time based on the estimated bio-information.

2. The apparatus of claim 1,
wherein the pulse wave sensor comprises:
a light source configured to emit light onto the object, and
a detector configured to detect the light reflected from the object; and
wherein the contact pressure sensor comprises:
a force sensor configured to measure a contact force of the object, and
an area sensor configured to measure a contact area of the object.

3. The apparatus of claim 1, wherein the processor is further configured to:
obtain a first feature based on the maximum amplitude value, a second feature based on the first contact pressure value and the second contact pressure value, and a third feature based on the third contact pressure value corresponding to the center of mass, and
estimate the bio-information by combining the first feature, the second feature, and the third feature.

4. The apparatus of claim 3, wherein the processor is further configured to assign a weight to each of the first feature, the second feature, and the third feature, and combines the first feature, the second feature, and the third feature based on the weight assigned to each of the first feature, the second feature, and the third feature.

5. The apparatus of claim 4, wherein the weight assigned to each of the first feature, the second feature, and the third feature is a preset fixed value or a value adjusted based on any one or any combination of characteristics and types of the bio-information.

6. The apparatus of claim 3, wherein the processor is further configured to:
extract a direct current (DC) component of the pulse wave signal, and
obtain a fourth feature based on a graph of the extracted DC component and the contact pressure.

7. The apparatus of claim 6, wherein the processor is further configured to:
perform curve fitting for the graph by using a fitting model, and
obtain a coefficient of the fitting model as the fourth feature, the coefficient being determined as a result of the curve fitting.

8. The apparatus of claim 6, wherein the processor is further configured to obtain any one or any combination of a maximum slope value, a contact pressure value at a maximum slope point, and a maximum amplitude value from the graph as the fourth feature.

9. The apparatus of claim 1, further comprising an output interface configured to output guide information on the contact pressure of the object based on a request for estimating the bio-information.

10. The apparatus of claim 9, wherein the object is a body part of a user, and
wherein the guide information comprises information for inducing the user to gradually increase the contact pressure or based on a determination that the contact pressure is greater than or equal to a predetermined threshold value, information for inducing the user to gradually decrease the contact pressure.

11. The apparatus of claim 1, wherein the object is a body part of a user, and
wherein the processor is further configured to:
determine a contact state between the object and the contact pressure sensor based on the contact pressure, and
based on determining that the contact state of the object is abnormal, guide the user to change the contact pressure.

12. The apparatus of claim 1, wherein the bio-information is blood pressure information.

13. A method of estimating bio-information, the method comprising:
obtaining, by a pulse wave sensor, a pulse wave signal from an object during a measurement period;
obtaining, by a contact pressure sensor, contact pressure of the object during the measurement period;
extracting a peak-to-peak amplitude of the pulse wave signal of each measurement time during the measurement period, by subtracting an amplitude value of a negative (−) point from an amplitude value of a positive (+) point of a waveform envelope of the pulse wave signal corresponding to the each measurement time;
obtaining an oscillometric envelope by plotting the extracted peak-to-peak amplitude of the pulse wave signal with respect to the contact pressure at the each measurement time;
determining a first contact pressure value and a second contact pressure value on the oscillometric envelope, each of the first contact pressure value and the second contact pressure value corresponding to a predetermined percentage of a maximum amplitude value of the oscillometric envelope;
obtaining a third contact pressure value corresponding to a center of mass of a region between the first contact pressure value and the second contact pressure value on the oscillometric envelope based on a weighted mean of the region;
estimating bio-information based on the third contact pressure value; and
outputting a notification in real-time based on the estimated bio-information.

14. The method of claim 13, wherein the estimating of the bio-information comprises obtaining a first feature based on the maximum amplitude value, a second feature based on the first contact pressure value and the second contact pressure value, and a third feature based on the third contact pressure value corresponding to the center of mass, and estimating the bio-information by combining the obtained first feature, the second feature, and the third feature.

15. The method of claim 14, wherein the estimating of the bio-information comprises assigning a weight to each of the first feature, the second feature, and the third feature, and combining the first feature, the second feature, and the third feature.

16. The method of claim 14, wherein the estimating of the bio-information further comprises extracting a direct current DC component of the pulse wave signal, and obtaining a fourth feature based on a graph of the extracted DC component and the contact pressure.

17. The method of claim 16, wherein the obtaining of the fourth feature comprises performing curve fitting for the graph by using a fitting model, and obtaining a coefficient of the fitting model, which is determined as a result of the curve fitting, as the fourth feature.

18. The method of claim 16, wherein the obtaining of the fourth feature comprises obtaining at least one of a maximum slope value, a contact pressure value at a maximum slope point, and a maximum amplitude value from the graph as the fourth feature.

19. The method of claim 13, further comprising outputting guide information on the contact pressure of the object based on a request for estimating the bio-information.

20. The method of claim 13, further comprising:
determining a contact state between the object and the contact pressure sensor based on the contact pressure; and
based on determining that the contact state of the object is abnormal, guiding a user to change the contact pressure,
wherein the object is a body part of the user.

* * * * *